US007951783B2

(12) United States Patent
Stauss et al.

(10) Patent No.: US 7,951,783 B2
(45) Date of Patent: May 31, 2011

(54) THERAPEUTICALLY USEFUL MOLECULES

(75) Inventors: Hans J. Stauss, London (GB); Liquan Gao, London (GB); Shao-An Xue, London (GB)

(73) Assignee: Imperial Innovations Limited, London (GB)

( * ) Notice: Subject to any disclaimer, the term of this patent is extended or adjusted under 35 U.S.C. 154(b) by 956 days.

(21) Appl. No.: 10/581,773

(22) PCT Filed: Dec. 6, 2004

(86) PCT No.: PCT/GB2004/005100
§ 371 (c)(1),
(2), (4) Date: Feb. 12, 2007

(87) PCT Pub. No.: WO2005/056595
PCT Pub. Date: Jun. 23, 2005

(65) Prior Publication Data
US 2007/0191496 A1    Aug. 16, 2007

(30) Foreign Application Priority Data
Dec. 6, 2003    (GB) .................................. 0328363.7

(51) Int. Cl.
A61K 48/00    (2006.01)
(52) U.S. Cl. ..................... 514/44 R; 435/325; 435/320.1
(58) Field of Classification Search ........................ None
See application file for complete search history.

(56) References Cited

FOREIGN PATENT DOCUMENTS
WO    WO 00/26249    5/2000

OTHER PUBLICATIONS

Stanislawski et al., Nat Immunol. Oct. 2001;2(10):962-70.*
Rudikoff et al., Proc. Natl. Acad. Sci. USA, 79:1979-1983, Mar. 1982.*
Vajdos et al., J Mol Biol. Jul. 5, 2002;320(2):415-28.*
Colman P. M., Research in Immunology, 145:33-36, 1994.*
Janeway, Immunobiology, 2001, Garland Publishing, pp. 262-263.*
Bellantuono et al., "Two Distinct HLA-A0201-Presented Epitopes of the Wilms Tumor Antigen 1 Can Function as Targets for Leukemia-Reactive CTL," Blood 100:3835-3837 (2002).
Boulter et al., "Stable, Soluble T-Cell Receptor Molecules for Crystallization and Therapeutics," Protein Eng. 16:707-711 (2003).
Chung et al., "Functional Three-Domain Single-Chain T-Cell Receptors," Proc. Natl. Acad. Sci. USA 91:12654-12658 (1994).
Dudley et al., "Cancer Regression and Autoimmunity in Patients After Clonal Repopulation with Antitumor Lymphocytes," Science 298:850-854 (2002).
Engels et al., "Retroviral Vectors for High-Level Transgene Expression in T Lymphocytes," Human Gene Ther. 14:1155-1168 (2003).
Eshhar et al., "Specific Activation and Targeting of Cytotoxic Lymphocytes Through Chimeric Single Chains Consisting of Antibody-Binding Domains and the γ or ζ Subunits of the Immunoglobulin and T-Cell Receptors," Proc. Natl. Acad. Sci. USA 90:720-724 (1993).
Finer et al., "*kat*: A High-Efficiency Retroviral Transduction System for Primary Human T Lymphocytes," Blood 83:43-50 (1994).
Gao et al., "Selective Elimination of Leukemic CD34+ Progenitor Cells by Cytotoxic T Lymphocytes Specific for WT1," Blood 95:2198-2203 (2000).
Gao et al., "Human Cytotoxic T Lymphocytes Specific for Wilms' Tumor Antigen-1 Inhibit Engraftment of Leukemia-Initiating Stem Cells in Non-Obese Diabetic-Severe Combined Immunodeficient Recipients," Transplantation 75:1429-1436 (2003).
Garcia et al., "Structural Basis of T Cell Recognition," Ann. Rev. Immunol. 17:369-397 (1999).
Hwu et al., "Lysis of Ovarian Cancer Cells by Human Lymphocytes Redirected with a Chimeric Gene Composed by an Antibody Variable Region and the Fc Receptor γ Chain," J. Exp. Med. 178:361-366 (1993).
Inoue et al., "Long-Term Follow-Up of Minimal Residual Disease in Leukemia Patients by Monitoring WT1 (Wilms Tumor Gene) Expression Levels," Blood 88:2267-2278 (1996).
Inoue et al., "Aberrant Overexpression of the Wilms Tumor Gene (WT1) in Human Leukemia," Blood 89:1405-1412 (1997).
Inoue et al., "Wilms' Tumor Gene (WT1) Competes with Differentiation-Inducing Signal in Hematopoietic Progenitor Cells," Blood 91:2969-2976 (1998).
Kast et al., "Eradication of Adenovirus E1-Induced Tumors by E1A-Specific Cytotoxic T Lymphocytes," Cell 59:603-614 (1989).
Kawakami et al., "Identification of a Human Melanoma Antigen Recognized by Tumor-Infiltrating Lymphocytes Associated with in vivo Tumor Rejection," Proc. Natl. Acad. Sci. USA 91:6458-6462 (1994).
Kessels et al., "Changing T Cell Specifically by Retroviral T Cell Receptor Display," Proc. Natl. Acad. Sci. USA 97:14578-14583 (2000).
Lefranc et al., "IMGT Unique Numbering for Immunoglobulin and T Cell Receptor Variable Domains and Ig Superfamily V-Like Domains," Dev. Comp. Immunol. 27:55-77 (2003).
Menssen et al., "Wilms' Tumor Gene (WT1) Expression in Lung Cancer, Colon Cancer and Glioblastoma Cell Lines Compared to Freshly Isolated Tumor Specimens," J. Cancer Res. Clin. Oncol. 126:226-232 (2000).
Menssen et al., "Presence of Wilms' Tumor Gene (WT1) Transcripts and the WT1 nuclear Protein in the Majority of Human Acute Leukemias," Leukemia 9:1060-1067 (1995).

(Continued)

*Primary Examiner* — Zachary Skelding
(74) *Attorney, Agent, or Firm* — Marshall, Gerstein & Borun LLP

(57) ABSTRACT

A T cell receptor molecule (TCR) containing an alpha chain portion and a beta chain portion wherein the alpha chain portion contains three complementarity determining regions (CDRs): CDR1α: SSYSPS CDR2α: YTSAATL CDR3α: VVSPF-SGGGADGLT or comprising or consisting of SPFSGGGADGLT and the beta chain portion contains three complementarity determining regions (CDRs): CDR1β: DFQATT CDR2β: SNEGSKA CDR3β: comprising SARDGGEG or comprising or consisting of RDGGEG-SETQY, or wherein up to three amino acid residues in one or more CDRs are replaced by another amino acid residue. The invention also includes polynucleotides encoding the TCR molecules, and host cells containing the said polynucleotides. Patient derived T cells may have the polynucleotides encoding the TCR molecules introduced therein, and the engineered T cells may be introduced into the patient in order to combat a WT1-expressing malignancy.

11 Claims, 16 Drawing Sheets

OTHER PUBLICATIONS

Menssen et al., "Detection by Monoclonal Antibodies of the Wilms' Tumor (WT1) Nuclear Protein in Patients with Acute Leukemia," Int. J. Cancer 70:518-523 (1997).

Miyoshi, "High Expression of Wilms' Tumor Suppressor Gene Predicts Poor Prognosis in Breast Cancer Patients," Clin. Cancer Res. 8:1167-1171 (2002).

Moritz et al., "Cytotoxic T Lymphocytes with a Grafted Recognition Specifically for ERBB2-Expressing Tumor Cells," Proc. Natl. Acad. Sci. USA 91:4318-4322 (1994).

Ogawa et al., "Successful Donor Leukocyte Transfusion at Molecular Relapse for a Patient with Acute Myeloid Leukemia Who Was Treated with Allogeneic Bone Marrow Transplantation: Importance of the Monitoring of Minimal Residual Disease by WT1 Assay," Bone Marrow Transplantation 21:525-527 (1998).

Oji et al., "Expression of the Wilms' Tumor Gene *WT1* in Solid Tumors and Its Involvement in Tumor Cell Growth," Jpn J. Cancer Res. 90:194-204 (1999).

Oji et al., "Overexpression of the Wilms' Tumor Gene *WT1* in Head and Neck Squamous Cell Carcinoma," Cancer Sci. 94:523-529 (2003).

Oji et al., "Overexpression of the Wilms' Tumor Gene *WT1* in Primary Thyroid Cancer," Cancer Sci. 94:606-611 (2003).

Oji et al., "Overexpression of the Wilms' Tumor Gene *WT1* in Colorectal Adenocarcinoma," Cancer Sci. 94:712-717 (2003).

Roberts et al., "Targeting of Human Immunodeficiency Virus-Infected Cells by CD8+ T Lymphocytes Armed with Universal T-Cell Receptors," Blood 84:2878-2889 (1994).

Rodeck et al., "Expression of the *WT1* Wilms' Tumor Gene by Normal and Malignant Human Melanocytes," Int. J. Cancer 59:78-82 (1994).

Silberstein et al., "Altered Expression of the WT1 Wilms Tumor Suppressor Gene in Human Breast Cancer," Proc. Natl. Acad. Sci. USA 94:8132-8137 (1997).

Stanislawski et al., "Circumventing Tolerance to a Human MDM2-Derived Tumor Antigen by TCR Gene Transfer," Nat. Immunol. 2:962-970 (2001).

Tamaki et al., "Increased Expression of Wilms Tumor Gene (WT1) at Relapse in Acute Leukemia," Blood 88:4396-4398 (1996).

Ueda et al., "Overexpression of the Wilms' Tumor Gene WT1 in Human Bone and Soft-Tissue Sarcomas," Cancer Sci. 94:271-276 (2003).

Viel et al., "Molecular Mechanisms Possibly Affecting WT1 Function in Human Ovarian Tumors," Int. J. Cancer 57:515-521 (1994).

Xue et al., "Elimination of Human Leukemia Cells in *NOD/SCID* Mice by *WT1-TCR* Gene-Transduced Human T Cells," Blood 106:3062-3067 (2005).

* cited by examiner

Figure 1:

Human TCR Vα-1.5 (Vα-8.2) coding sequence

ATGCTCCTGC TGCTCGTCCC AGTGCTCGAG GTGATTTTTA CTCTGGGAGG
AACCAGAGCC CAGTCGGTGA CCCAGCTTGA CAGCCACGTC TCTGTCTCTG
AAGGAACCCC GGTGCTGCTG AGGTGCAACT ACTCATCTTC TTATTCACCA
TCTCTCTTCT GGTATGTGCA ACACCCCAAC AAAGGACTCC AGCTTCTCCT
GAAGTACACA TCAGCGGCCA CCCTGGTTAA AGGCATCAAC GGTTTTGAGG
CTGAATTTAA GAAGAGTGAA ACCTCCTTCC ACCTGACGAA ACCTCAGCC
CATATGAGCG ACGCGGCTGA GTACTTCTGT GTTGTGAGTC CTTTTCAGG
AGGAGGTGCT GACGGACTCA CCTTTGGCAA AGGGACTCAT CTAATCATCC
AGCCCTATAT CCAGAACCCT GACCCTGCCG TGTACCAGCT GAGAGACTCT
AAATCCAGTG ACAAGTCTGT CTGCCTATTC ACCGATTTTG ATTCTCAAAC
AAATGTGTCA CAAAGTAAGG ATTCTGATGT GTATATCACA GACAAAACTG
TGCTAGACAT GAGGTCTATG GACTTCAAGA GCAACAGTGC TGTGGCCTGG
AGCAACAAAT CTGACTTTGC ATGTGCAAAC GCCTTCAACA ACAGCATTAT
TCCAGAAGAC ACCTTCTTCC CCAGCCCAGA AGTTCCTGT GATGTCAAGC
TGGTCGAGAA AAGCTTTGAA ACAGATACGA ACCTAAACTT TCAAACCTG
TCAGTGATTG GGTTCCGAAT CCTCCTCCTG AAAGTGGCCG GGTTTAATCT
GCTCATGACG CTGCGGCTGT GGTCCAGCTG A

Figure 2

Human TCR Vα-1.5 (Vα-8.2) protein sequence

FR1
MLLLLVPVLEVIFTLGGTRAQSVTQLDSHVSVSEGT

CDR1
PVLLRCNYSSSYSPSLFWYVQHPNKGLQLLLKYT

FR2

CDR2
SAATLVKGINGFEAEFKKSETSFHLTKPSAHMSDA

FR3

CDR3
AEYFCVVSPFSGGGADGLT constant
FGKGTH LIIQPYIQNP DPAVYQLRDSKSSDKSVCLF
TDFDSQTNVS QSKDSDVYIT DKTVLDMRSM
DFKSNSAVAWSNKSDFACAN AFNNSIIPED
TFFPSPESSCDVKLVEKSFETDTNLNFQNLSVIGFRIL
LL KVAGFNLLMT LRLWSS

Figure 3:

Human TCR Vβ-2.1 (Vβ-20.1) coding sequence

ATGCTGCTGC TTCTGCTGCT TCTGGGGCCA GGCTCCGGGC TTGGTGCTGT
CGTCTCTCAA CATCCGAGCT GGGTTATCTG TAAGAGTGGA ACCTCTGTGA
AGATCGAGTG CCGTTCCCTG GACTTTCAGG CCACAACTAT GTTTTGGTAT
CGTCAGTTCC CGAAACAGAG TCTCATGCTG ATGGCAACTT CCAATGAGGG
CTCCAAGGCC ACATACGAGC AAGGCGTCGA GAAGGACAAG TTTCTCATCA
ACCATGCAAG CCTGACCTTG TCCACTCTGA CAGTGACCAG TGCCCATCCT
GAAGACAGCA GCTTCTACAT CTGCAGTGCT AGAGATGGGG GGGAGGGTC
GGAGACCCAG TACTTCGGGC CAGGCACGCG GCTCCTGGTG CTCGAGGACC
TGAAAAACGT GTTCCCACCC GAGGTCGCTG TGTTTGAGCC ATCAGAAGCA
GAGATCTCCC ACACCCAAAA GGCCACACTG GTGTGCCTGG CCACAGGCTT
CTACCCCGAC CACGTGGAGC TGAGCTGGTG GGTGAATGGG AAGGAGGTGC
ACAGTGGGGT CAGCACAGAC CCGCAGCCC TCAAGGAGCA GCCCGCCCTC
AATGACTCCA GATACTGCCT GAGCAGCCGC CTGAGGGTCT CGGCCACCTT
CTGGCAGAAC CCCCGCAACC ACTTCCGCTG TCAAGTCCAG TTCTACGGGC
TCTCGGAGAA TGACGAGTGG ACCCAGGATA GGGCCAAACC TGTCACCCAG
ATCGTCAGCG CCGAGGCCTG GGGTAGAGCA GACTGTGGCT TCACCTCCGA
GTCTTACCAG CAAGGGGTCC TGTCTGCCAC CATCCTCTAT GAGATCTTGC
TAGGGAAGGC CACCTTGTAT GCCGTGCTGG TCAGTGCCCT CGTGCTGATG
GCCATGGTCA AGAAAAGGA TTCCAGAGGC TAG

Figure 4

Human TCR Vβ-2.1 (Vβ-20.1) protein sequence

FR1
MLLLLLLGPGSGLGAVVSQHPSWVICKSGTSVKIECR

CDR1
SLDFQATTMFWYRQFPKQSLMLMATSNEGSKATYEQ

FR2

CDR2

FR3
GVEKDKFLINHASLTLSTLTVTSAHPEDSSFYICSARD

CDR3
GGEG constant
SETQYFGPGTRLLVLEDLKNVFPPEVAVFEPSEAEISHTQ
KATLVCLATGFYPDHVELSWWVNGKEVHSGVSTDPQPL
KEQPALNDSRYCLSSRLRVSATFWQNPRNHFRCQVQFY
GLSENDEWTQDRAKPVTQIVSAEAWGRADCGFTSESYQ
QGVLSATILYEILLGKATLYAVLVSALVLMAMVKRKDS
RG

Figure 5

Human TCR Vα-1.5 (Vα-8.2) protein sequence

FR1
MLLLLVPVLEVIFTLGGTRAQSVTQLDSHVSVSEGT

CDR1
PVLLRCNYSSSYSPSLFWYVQHPNKGLQLLLKYT

FR2

CDR2
SAATLVKGINGFEAEFKKSETSFHLTKPSAHMSDA

FR3

Va8.2

CDR3
AEYFCVVSPFSGGGADGLTFGKGTH LIIQP

J45 constant
YIQNP DPAVYQLRDSKSSDKSVCLF TDFDSQTNVS
QSKDSDVYIT DKTVLDMRSM
DFKSNSAVAWSNKSDFACAN AFNNSIIPED
TFFPSPESSCDVKLVEKSFETDTNLNFQNLSVIGFRIL
LL KVAGFNLLMT LRLWSS

Human TCR Vβ-2.1 (Vβ-20.1) protein sequence

FR1
MLLLLLLLGPGSGLGAVVSQHPSWVICKSGTSVKIECR

CDR1
SLDFQATTMF

FR2
WYRQFPKQSLMLMATSNEGSKATYEQ

CDR2
GVEKDKFLINHASLTLSTLTVTSAHPEDSSFYICSARD

FR3
GGEGSETQYFGPGTRLLVL

CDR3
J2.5

Constant 2
EDLKNVFPPEVAVFEPSEAEISHTQKATLVCLATGFYPDH
VELSWWVNGKEVHSGVSTDPQPLKEQPALNDSRYCLSS
RLRVSATFWQNPRNHFRCQVQFYGLSENDEWTQDRAKP
VTQIVSAEAWGRADCGFTSESYQQGVLSATILYEILLGK
ATLYAVLVSALVLMAMVKRKDSRG figure 6

TCR transduced bulk T cells show pWT126-specific killing activity

TCR transduced CD8+ T cells show pWT126-specific IFN-γ production

THERAPEUTICALLY USEFUL MOLECULES

The present invention relates to therapeutically useful molecules, in particular to T cell receptors (TCRs) which may be introduced into a patient's own T cells in order to direct the T cells to kill cancer cells within the patient, particularly cancer cells which express the Wilms Tumour antigen-1 (WT1).

The listing or discussion of a prior-published document in this specification should not necessarily be taken as an acknowledgement that the document is part of the state of the art or is common general knowledge. All of the documents referred to in this specification are hereby incorporated by reference.

There is evidence that anti-tumour cytotoxic T lymphocytes (CTL) play an important role in vivo. Tumour reactive CTL have been shown to mediate tumour regression in animal models (Kast et al (1989) *Cell* 59, 603-614) and in man (Kawakami et al (1994) *Proc. Natl. Acad Sci. USA* 91, 6458-6462; Dudley (2002) *Science* 298, 850-854). As with all types of anti-tumour therapy, a problem that needs to be overcome is that the therapy must destroy or inactivate the target tumour cells to a useful extent but that the therapy must not destroy or inactivate non-tumour cells to a deleterious extent. In other words, it is desirable if the therapy is selective for tumour cells to a beneficial extent.

Much of the current work on immunotherapy of cancer makes use of the fact that certain tumours express polypeptides which are not expressed in the equivalent non-tumour tissue, or makes use of the fact that the tumour expresses a mutant form of a polypeptide which is not expressed in the non-tumour tissue. However, it is not always possible to identify polypeptides in a tumour which fall into this category, and so other target polypeptides which can form the basis of an immunotherapeutic approach have been identified.

In adults, expression of WT1, an embryonic transcription factor, has been observed in renal podocytes, in the testis, in the ovary, in breast myoepithelial cells and in some CD34[+] stem cells in the bone marrow. Aberrant expression was observed in breast cancer, ovarian cancer, melanoma, lung cancer, colon cancer, thyroid cancer, head and neck cancer, glioblastoma, sarcoma and leukaemia including CML and AML (see, for example, Menssen et al (1995) *Leukaemia* 9, 1060-1067; Inoue et al (1997) *Blood* 89, 1405-1412; Inoue et al (1996) *Blood* 88, 2267-2278; Inoue et al (1998) *Blood* 91, 2969-2976; Menssen et al (1997) *Int. J Cancer* 70, 518-523; Menssen et al (1995) *Leukemia* 9, 1060-1067; Ogawa et al (1998) *Transplant* 21, 527-527; Rodeck et al (1994) *Int. J Cancer* 59, 78-82; Silberstein et al (1997) *Proc. Natl. Acad Sci. USA* 94, 8132-8137; Tamaki et al (1996) *Blood* 88, 43964398; Viel et al (1994) *Int. J Cancer* 57, 515-521; Menssen (2000) *J. Cancer Res. Clin. Oncol.* 126, 226-232; Miyoshi (2002) *Clin. Cancer Res.* 8, 1167-1171; Oji (1999) *Jpn J. Cancer Res.* 90, 194-204; Oji (2003) *Cancer Sci.* 94, 523-529; Oji et al (2003) *Cancer Sci.* 94, 606-611; Oji et al (2003) *Cancer Sci.* 94, 712-717; and Ueda (2003) *Cancer Sci.* 94, 271-276.

As described in our patent application WO00/26249, using an unconventional approach employing allo-MHC-restricted CTL, we identified peptide epitopes in the WT1 polypeptide which may be presented by HLA-A2 class I molecules and displayed on the surface of tumour cells expressing these proteins endogenously. HLA-A2 negative responder individuals were used as a source of CTL specific for peptides presented by HLA-A2 class I molecule, and this approach allows identification of HLA-A2 presented peptides independent of possible tolerance of autologous CTL.

One of the peptide epitopes disclosed in WO00/26249 is RMFPNAPYL (SEQ ID NO: 1) (which we have also termed pWT126), and we have previously described a CTL which is able to: kill HLA-A2-positive targets coated with the WT1-derived peptide pWT126 (Gao et al (2000) *Blood* 95, 2198-2203); kill fresh HLA-A2-positive leukaemia cells expressing WT1 (Gao et al (2000) *Blood* 95, 2198-2203); kill HLA-A2-positive leukemia CFU progenitor cells (Gao et al (2000) *Blood* 95, 2198-2203; Bellantuono et al (2002) *Blood* 100, 3835-3837); kill HLA-A2-positive leukaemia LTC-IC stem cells (Bellantuono et al (2002) *Blood* 100, 3835-3837); kill HLA-A2-positive NOD/SCID leukaemia initiating cells (Gao et al (2003) *Transplantation* 75, 1429-1436); and do not kill normal HLA-A2-positive NOD/SCID engrafting hematopoietic stem cells (Gao et al (2003) *Transplantation* 75, 1429-1436). However, none of these publications give molecular information concerning the TCR present in the CTL, and the particular CTL line mentioned in the publications has not been made available to the public in any way and so the structure of the TCR is unknown and could not be derived by the skilled person (since the CTL line was not publicly available).

The present inventors have now cloned a TCR that is specific to RMFPNAPYL (SEQ ID NO: 1), a peptide of WT1 which is presented by HLA-A2 class I molecules, and have shown that introducing the TCR into either CD4-positive or CD8-positive T cells confers on the engineered T cells the ability to kill cancer cells which express WT1 endogenously. In addition, the inventors have defined the molecular structure of the TCR, identified the complementarity determining (CDRs), and describe how to make recombinant TCRs which are believed to retain the same specificity of the parent molecule.

The TCRs may usefully be introduced into a T cell derived from a patient (preferably an HLA-A2-positive patient) suffering from a malignancy (where the patient's tumour cells express WT1), and the engineered T cell introduced into the patient in order to combat the malignancy. In particular, it is proposed to take T cells from patients with breast cancer, colon cancer, lung cancer, other solid cancers or leukaemia, transduce them in vitro with a retroviral vector containing the TCR genes, and re-infuse the transduced T cells into the patients. The credibility of this approach is confirmed by the demonstration in the Examples that the WT1-specific TCR genes can be transferred into human T cells, that the genes give raise to TCR expression on the surface of recipient T cells, that the recipient T cells can kill HLA-A2-positive target cells coated with the pWT126 peptide and HLA-A2-positive tumour cells expressing WT1 endogenously.

The general structure of T cell receptors (TCRs), their domain structure and the organisation of genes that encode them is well known, for example see Chapter 11 in Immunology, second edition (1994), by Janis Kuby, W H Freeman & Co, New York, USA, and Garcia et al (1999) *Ann. Rev. Immunol.* 17, 369-397. One common class of natural TCRs is the αβ class in which the TCRs are made up of a separate alpha chain and a separate beta chain which form a heterodimer which is T cell membrane associated. Each alpha and beta chain is made up of regions which, in order from the N terminus to the C terminus are a leader sequence, a variable region, a constant region, a connecting sequence, a transmembrane region and a cytoplasmic tail region (see FIG. 14 for a graphical representation of αβ TCR structure). The variable region of the alpha chain is called the Vα region and the variable region of the beta chain is called the Vβ region. Similarly, the constant region of the alpha chain is called the Cα region and the constant region of the beta chain is called the Cβ region. The job of the αβ TCR is to recognise and bind to a peptide presented in a HLA molecule of a cell in the body. Generally speaking, the TCR cannot recognise and bind the peptide unless it is presented by a particular HLA molecule, and the TCR cannot recognise a HLA molecule unless it is presenting the specific peptide. T cells harboring a specific TCR will target cells which are presenting a specific peptide in a particular HLA molecule on a cell (ie a peptide-HLA complex), and this is the main principle of T cell-based immunity.

The peptide-HLA complex is recognised by the combined V regions of the alpha and beta chains of the TCR In particular, it is the complementarity determining regions (CDRs) of the V regions which mediate recognition of the peptide-HLA complex. The V region of the alpha and beta chains of the natural TCR are made up of, in order in an N-terminal to C-terminal direction, FR1, CDR1, FR2, CDR2, FR3 and CDR3, where FR stands for "framework region" and CDR stands for "complementarity determining region". The FRs and CDRs of the alpha and beta chains are different.

From the predicted amino acid sequences of the alpha and beta chains of the TCR cloned as mentioned above, the inventors have determined the FRs and CDRs of the alpha and beta chains (see FIGS. 2 and 4). With the knowledge of the CDR sequences, it is possible to produce chimaeric TCRs in which the CDRs are grafted onto framework regions with which the CDRs are not naturally associated, and it is also possible to produce single chain TCR molecules, and in both cases the molecules retain substantially the same binding affinity for the peptide-HLA complex as the parent molecule, as is described in more detail below.

A first aspect of the invention provides a cell receptor (TCR) molecule containing an alpha chain portion and a beta chain portion wherein the alpha chain portion contains three complementarity determining regions (CDRs):

CDR1α: SSYSPS (SEQ ID NO: 2)
CDR2α: YTSAATL (SEQ ID NO: 3)
CDR3β: VVSPFSGGGADGLT (SEQ ID NO: 4) or comprising or consisting of SPFSGGGADGLT (SEQ NO: 5) and the beta chain portion contains three complementarity determining regions (CDRs):
CDR1β: DFQATT (SEQ ID NO: 6)
CDR2β: SNEGSKA (SEQ ID NO: 7)
CDR3β: comprising SARDGGEG (SEQ ID NO: 8), or comprising or consisting of RDGGEGSETQY (SEQ ID NO: 9) or wherein up to three amino acid residues in one or more of the CDRs are replaced by another amino acid residue.

It should be noted that in some nomenclature systems the CDR3 of the β chains may be defined to be longer than in the nomenclature system used in the Immunogenetics (IMGT) database described below. Also, in some nomenclature systems the CDR3 of the α chains may be defined to be shorter than in the IMGT system. Similarly, the constant portion may or may not include framework residues flanking the CDR3 region in the different nomenclature systems.

Thus, in one embodiment using the IMGT system CDR3α may have the amino acid sequence VVSPFSGGGADGLT (SEQ ID NO: 4) and the constant portion includes the framework amino acid sequence FGKGTHLIIQP (SEQ ID NO: 10) (see FIG. 5).

In another embodiment, using the Garcia nomenclature system (Garcia et al (1999) Ann. Rev. Immunol. 17, 369-397, incorporated herein by reference) CDR3α comprises or consists of the amino acid sequence SPFSGGGADGLT (SEQ ID NO: 5), the framework region immediately C-terminal to this has the amino acid sequence FGKGTHLIIQP (SEQ ID NO: 10) and the constant region begins with the amino acid sequence YIQNP (SEQ ID NO: 11) . . . (see FIG. 5).

In one embodiment using the IMGT nomenclature system, CDR3β may have the amino acid sequence SARDGGEG (SEQ ID NO: 8) and the constant region immediately C-terminal to this includes the framework amino acid sequence SETQY (SEQ ID NO: 12) . . . (FIG. 4).

In another embodiment, using the Garcia nomenclature system as above, CDR3β comprises or consists of the amino acid sequence RDGGEGSETQY (SEQ ID NO: 9) and the framework region immediately C-terminal to this has the amino acid sequence FGPGTRLLVL (SEQ ID NO: 13) and the immediately C-terminal constant region begins with the amino acid sequence EDLKN (SEQ ID NO: 14) . . . (see FIG. 6).

It will be appreciated that the skilled person can readily design and synthesise TCRs according to the invention using either or any nomenclature systems provided that the framework region (ie region not replaced by the CDRs) is compatible with the CDRs as is well known in the act.

The standard IUPAC one letter amino acid code is used throughout the specification. For the avoidance of doubt, a reference to a "particular" or "given" CDR means any CDR with the amino acid sequence given above or wherein up to three amino acids have been replaced by another amino acid residue.

By "TCR molecule" we include any molecule which contains the given CDRs and also contains FRs suitably situated within the molecule so that the CDRs form a recognition site (combining site) which is able to bind to HLA-A2 presenting the peptide RMFPNAPYL (SEQ ID NO: 1) (ie a HLA-A2/RMFPNAPYL (SEQ ID NO: 1) complex).

It is particularly preferred if the TCR molecules contain the precise CDR amino acid sequences as given above and in FIGS. 2 and 4 and in FIGS. 5 and 6. Where a variant to this precise sequence is present, it preferably varies by one or two or three (preferably one or two) amino acids in one or two or three or four or five or all six CDRs. Typically, in these variants, the amino acids which are replaced are replaced with conservative amino acids. By conservative amino acids we include the groupings: G, A; S, A, T; F, Y, W; D, E; N, Q; and I, L, V.

A method for making and selecting TCR molecules which have CDRs which vary from the precise CDR sequences given in FIGS. 2 and 4 and in FIGS. 5 and 6 is given below.

The amino acid sequences, including V regions (and therefore FRs), of numerous TCR alpha chains and TCR beta chains are well known in the art, some of which are described in the IMGT (Immunogenetics) database at http://imgt-.cines.fr. See also Lefranc (2003) Dev. Comp. Immunol. 27, 55-77. The structural basis of T cell recognition is reviewed in Garcia et al (1999) Ann. Rev. Immunol. 17, 369-397, and the information contained therein may be used to design and synthesise CDR-grafted TCRs (and CDRs defined on the basis of this nomenclature are noted above). Preferably, the FRs into which the particular CDRs are grafted are FRs of human TCR alpha or beta chains. Conveniently, the alpha chain CDRs are grafted into alpha chain FRs, and beta chain CDRs are grafted to beta chain FRs. Typically, the three CDRs in the alpha chain and the three CDRs in the beta chain replace, in order, CDRs in other human alpha and beta chains, respectively. See Lefranc (2003) Dev. Comp. Immunol. 27, 55-77.

Typically, T cells expressing the TCR molecule recognise the HLA-A2 presenting peptide RMFPNAPYL (SEQ ID NO: 1) with substantially the same avidity as the TCR molecule which consists of the alpha and beta chains as described in FIGS. 2 and 4. This can be measured by retroviral-mediated transfer of the TCR into T cells followed by peptide titration experiments with the TCR-transduced T cells as outlined, for example, in Gao et al (2000) *Blood* 95, 2198-2203.

The TCR molecule preferably contains an alpha chain portion containing, in N-terminal to C-terminal order, FR1α-CDR1α-FR2α-CDR2α-FR3α-CDR3α, and a beta chain portion containing, in N-terminal to C-terminal order, FR1β-CDR1β-FR2β-CDR2β-FR3β-CDR3β as shown in FIGS. 2 and 4, respectively and in FIGS. 5 and 6, respectively. Typically, the TCR molecule contains the V region of both the alpha chain and the beta chain of the TCR polypeptide chains shown in FIGS. 2 and 4, and in FIGS. 5 and 6.

In a preferred embodiment, the alpha chain portion and the beta chain portion are present on different polypeptide chains. Typically, the TCR molecule contains an alpha chain which contains the V region and the C region of the polypeptide chain shown in FIG. 2 (or FIG. 5), and also contains a beta chain which contains the V region and C region of the polypeptide chain shown in FIG. 4 (or FIG. 6). Preferably, the TCR molecule consists of a molecule containing the complete alpha chain shown in FIG. 2 and the complete beta chain shown in FIG. 4. Typically, however, the leader sequence is cleaved off the mature alpha chain and beta chain.

In a further embodiment, the alpha chain portion and the beta chain portion of the TCR molecule are present in the same polypeptide chain. Single chain TCR molecules are described in Chung et al (1994) *Proc. Natl. Acad Sci. USA* 91, 12654-12658, and the principles described therein may readily be applied to the production of single chain TCR molecules which contain the specified CDRs. Typically, the single chain TCR molecules contain the Vα, Vβ and Cβ domains fused in the same polypeptide chain, and typically in that order (from N-terminus to C-terminus). For expression of a single chain TCR it is useful to provide a construct encoding the constant domain of the TCR alpha chain.

An additional strategy is described in Boulter et al 2003) *Protein Eng.* 16, 707-711 in which a new disulphide bond is introduced between a threonine in the constant region of the alpha chain and a serine in the constant region of the beta chain (by replacing these residues with a cysteine. The disulphide bond in the TCR connecting peptide may be removed or may remain in place.

The two-chain TCR molecules of the invention (eg ones which contain the alpha and beta chains whose amino acid sequence is given in FIGS. 2 and 4) or chimaeric TCRs which contain the specific CDRs as described above may be used to introduce to create antigen-specific CTL as described in more detail below (by using polynucleotides that encode the relevant chains). Similarly, the single chain TCRs may also be used for this purpose, and have the advantage that they do not pair with endogenous TCRs. Single chain TCRs may also be used as soluble constructs in a way similar to antibodies. In this case, the single chain constructs do not contain a transmembrane region (see Chung et al supra and Boulter et al supra).

A second aspect of the invention provides a polynucleotide encoding the alpha chain portion as defined in the first aspect of the invention. A third aspect of the invention provides a polynucleotide encoding the beta chain portion as defined in the first aspect of the invention. As discussed above, in a particularly preferred embodiment of the invention, the alpha chain portion and the beta chain portion are present on different polypeptide chains, and it is convenient (but not mandatory) that each polypeptide is encoded by a separate polynucleotide. Preferred polynucleotides encoding the alpha and beta chains are described in FIGS. 1 and 2, respectively.

Alternatively, the two polypeptides may be encoded on the same polynucleotide, in which case the two coding regions may be linked by an (Internal Ribosome Entry Site) IRES sequence, and typically would have its own translational start and stop codons. Typically, such constructs contain two promoters, one for each TCR chain.

As discussed above, in an alternative embodiment the alpha chain portion and the beta chain portion are present in the same polypeptide, in which case a single polynucleotide may encode the single chain polypeptide.

In any event, the polynucleotide may be DNA or RNA, and it may or may not contain introns. Typically, the polynucleotide does not contain introns within the region that codes for the polypeptide of interest. It will be appreciated that different polynucleotides may encode the same polypeptide because of the degeneracy of the genetic code.

The invention also provides an expression vector that contains the polynucleotide of the invention. Such expression vectors, when present in a suitable host cell, allow for the expression of the polypeptide(s) of interest. Preferably, the expression vector is an expression vector capable of expressing a polypeptide in a mammalian cell. More preferably, the expression vector is one which is able to express a polypeptide in a T cell, such as a human CTL. Typically, the expression vectors contain a promoter which is active in particular cell types, and which may be controllable (eg inducible).

The vector is suitably a retroviral vector which is capable of transfection into a mammalian host cell such as a human T cell. Typically, the vector is a lentiviral vector.

A further aspect of the invention provides a host cell comprising a polynucleotide of the invention or a vector of the invention. The host cell may contain a polynucleotide or vector which encodes only the alpha chain portion or only the beta chain portion. However, if the host cell is to produce a TCR molecule of the invention, it contains one or more polynucleotides or vectors which encode both the alpha chain portion and the beta chain portion.

The host cell may be any cell such as a bacterial cell, yeast cell, insect cell, plant cell or mammalian cell, and methods of introducing polynucleotides into such cells are well known in the art. Typically, bacterial cells, such as *Escherichia coli* cells are used for general propagation and manipulation of the polynucleotides and vectors of the invention. Other host cells may be used to express the TCR molecules of the invention and, in particular, the cell may be a mammalian cell such as a human cell. As described below in relation to the therapeutic methods using the TCR molecules of the invention, it is particularly desirable if the host cell is a T cell such as (and preferably) a T cell derived from a patient to be treated, typically a patient with a WT1-expressing malignancy.

Typically, a retroviral vector (or, as the case may be vectors) encoding the TCR molecule of the invention is used based on its ability to infect mature human $CD4^+$ or $CD8^+$ T lymphocytes and to mediate gene expression: the retroviral vector system Kat is one preferred possibility (see Finer et al (1994) *Blood* 83, 43). High titre amphotrophic retrovirus are used to infect purified $CD8^+$ T lymphocytes isolated from the peripheral blood of tumour patients following a protocol published by Roberts et al (1994) *Blood* 84, 2878-2889, incorporated herein by reference. Anti-CD3 antibodies are used to trigger proliferation T cells, which facilitates retroviral integration and stable expression of single chain TCRs. A combination of anti-CD3 and anti-CD8 antibodies may be more effective than anti-CD3 antibodies alone. Other suitable systems for introducing genes into CTL are described in Moritz et al (1994) *Proc. Natl. Acad. Sci. USA* 91, 4318-4322, incorporated herein by reference. Eshhar et al (1993) *Proc. Natl.*

*Acad Sci. USA* 90, 720-724 and Hwu et al (1993) *J. Exp. Med.* 178, 361-366 also describe the transfection of CTL. The commercially available Nuclofactor system, provided by AMAXA, Germany may be used to transfect T cells. Retroviral transduction of human CD8+ T cells is described in Stanislawski (2001) *Nat. Immunol.* 2, 962.

Methods of cloning and genetic manipulation are well known in the art and are described in detail in standard manuals such as Sambrook & Russell (2001) Molecular Cloning, a laboratory manual, Cold Spring Harbor Press, Cold Spring Harbor, N.Y., USA.

Patients suffering from a WT1-expressing malignancy may be treated by the introduction of the TCR molecule of the invention into their own T cells (or T cells from a donor), followed by the introduction of these engineered cells into the patient. Thus, a further aspect of the invention provides a method of combating a WT-1 expressing malignancy in a patient, the method comprising introducing into the patient a T cell, preferably derived from the patient, which is modified to express the TCR molecule of the invention. Typically, (1) T cells are obtained from the patient, (2) a polynucleotide or polynucleotides encoding and capable of expressing the TCR molecule of the invention are introduced into the T cells ex vivo and (3) the engineered T cells are introduced into the patient. It is particularly preferred if the T cells are the patient's T cells (ie autologous).

It is particularly preferred if the patient is HLA-A2 positive.

In other words, the specificity of the T cell, preferably autologous T cell, is changed by the introduction of the TCR molecule of the invention.

The T cells (for example of the patient) are typically isolated from peripheral blood mononuclear cells (PBMCs), and may be CD4+ and CD8+ cells. Typically, the cells are activated using an antibody (eg an anti-CD3 or anti-CD28 antibody) so that they become receptive to transfection, for example with one or more retroviral vectors encoding the TCR molecules of the invention. The number of cells isolated, transfected and returned to the patient may be determined by the physician.

Cells may be taken from a patient after a clinical response, cryopreserved, transfected and re-infused if the same patient relapses.

Whether or not a malignancy is one which expresses WT1 may be determined, for example using reverse transcriptase-polymerase chain reaction (RT-PCR) or using intracellular staining techniques for the WT1 protein (which may be anti-WT1 antibodies).

The patient is preferably a human patient although animals may be used in a research situation. It is particularly preferred that the patient is HLA-A2 positive. Whether or not a patient is HLA-A2 positive can be determined by methods well known in the art.

Typically, the patient is suffering from any one or more of leukaemia, breast cancer, colon cancer, lung cancer, ovarian cancer, melanoma, thyroid cancer, head and neck cancer, glioblastoma, and sarcoma.

A further aspect of the invention provides the use of a T cell, preferably a patient derived T cell, which is modified to express the TCR molecule of the invention in the manufacture of a medicament for combating a WT1-expressing malignancy in the patient.

As discussed above, TCR molecules in which one or more of the CDRs differ in sequence from the precise CDR sequences given in FIGS. 2 and 4 form part of the invention. Preferably, such TCR molecules are able to recognise the HLA-A2/RMFPNAPYL (SEQ ID NO: 1) complex more effectively than a TCR molecule with the precise CDR sequences. Thus, a further aspect of the invention provides a method of selecting a TCR molecule with improved binding to an HLA-A2/RMFPNAPYL (SEQ ID NO: 1) complex comprising (a) providing a TCR molecule containing an alpha chain portion and a beta chain portion wherein the alpha chain portion contains three complementarity determining regions (CDRs):

CDR1α: SSYSPS (SEQ ID NO: 2)
CDR2β: YTSAATL (SEQ ID NO: 3)
CDR3α: VVSPFSGGGADGLT (SEQ ID NO: 4) or comprising or consisting of SPFSGGGADGLT (SEQ ID NO: 5) and the beta chain portion contains three complementarity determining regions (CDRs):
CDR1β: DFQATT (SEQ ID NO: 6)
CDR2β: SNEGSKA (SEQ ID NO: 7)
CDR3β: comprising SARDGGEG (SEQ ID NO: 8) or comprising or consisting of RDGGEGSETQY (SEQ ID NO: 9) wherein at least one amino acid residue in one or more of the CDRs as given is replaced with another amino acid residue, (b) determining whether the TCR molecule binds to an HLA-A2/RFMPNAPYL (SEQ ID NO: 1) complex with greater affinity than a TCR molecule without the replacement amino acid(s), and (c) selecting a molecule which binds with greater affinity. Preferably, the CDR3β has the amino acid sequence given above in relation to the first aspect of the invention.

TCR molecules with altered CDRs can readily be made by protein engineering methods. For example, a TCR display library may be made in which the alpha chain and/or beta chain CDR regions are mutagenised and the TCR molecules displayed using retroviral transduction on the surface of a T cell lymphoma (see Kessels et al (2000) Proc. Natl. Acad. Sci. USA 97, 14578-14583), or on the surface of a yeast or a bacteriophage. A HLA-A2/RMPNAPYL (SEQ ID NO: 1) complex may be used to select cells or bacteriophages which bind the complex with high affinity by virtue of the TCR molecule that they present. TCR molecules which have a higher binding affinity (lower $K_D$) than a TCR molecule with the precise CDR sequences are selected for further study.

The invention will now be described in more detail by reference to the following figures and non-limiting examples.

FIG. 1 shows the nucleotide coding sequence or the pWT126-specific TCR-alpha chain (Vα-1.5) (SEQ ID NO: 15).

FIG. 2 shows the protein sequence of the pWT126-specific TCR-alpha chain (Vα-1.5). The position of the CDRs, FRs and constant region are marked. The leader sequence is shown in bold (SEQ ID NO: 16).

FIG. 3 shows the nucleotide coding sequence of the pWT126-specific TCR-beta chain (Vβ-2.1) (SEQ ID NO: 17).

FIG. 4 shows the protein sequence of the pWT126-specific TCR-beta chain (V.beta.-2.1). The position of the CDRs, FRs and constant region are marked (SEQ ID NO: 18).

FIG. 5 shows the same protein sequence as in FIG. 2 (SEQ ID NO: 16) but the start position of the constant region is indicated to be in a different place. The CDR sequence in this figure, starting after C, is based on IMGT nomenclature (primary sequence based). The Garcia nomenclature is based on structure and does not include the VV after the C (ie it starts SPF . . . ). Vα8.2 means variable alpha 8.2 gene segment and J45 means joining 45 gene segment.

FIG. 6 shows the same protein sequence as in FIG. 4 (SEQ ID NO: 18) except that CDR3β is indicated as being longer and the start position of the constant region is indicated to be in a different place. The CDR sequence in this figure, starting after C, is based on IMGT nomenclature (primary sequence based). The Garcia nomenclature is based on structure and does not include the SA after the C (ie it starts RDGG . . . ). J2.5 refers to joining 2.5 gene segment.

Figure 7:
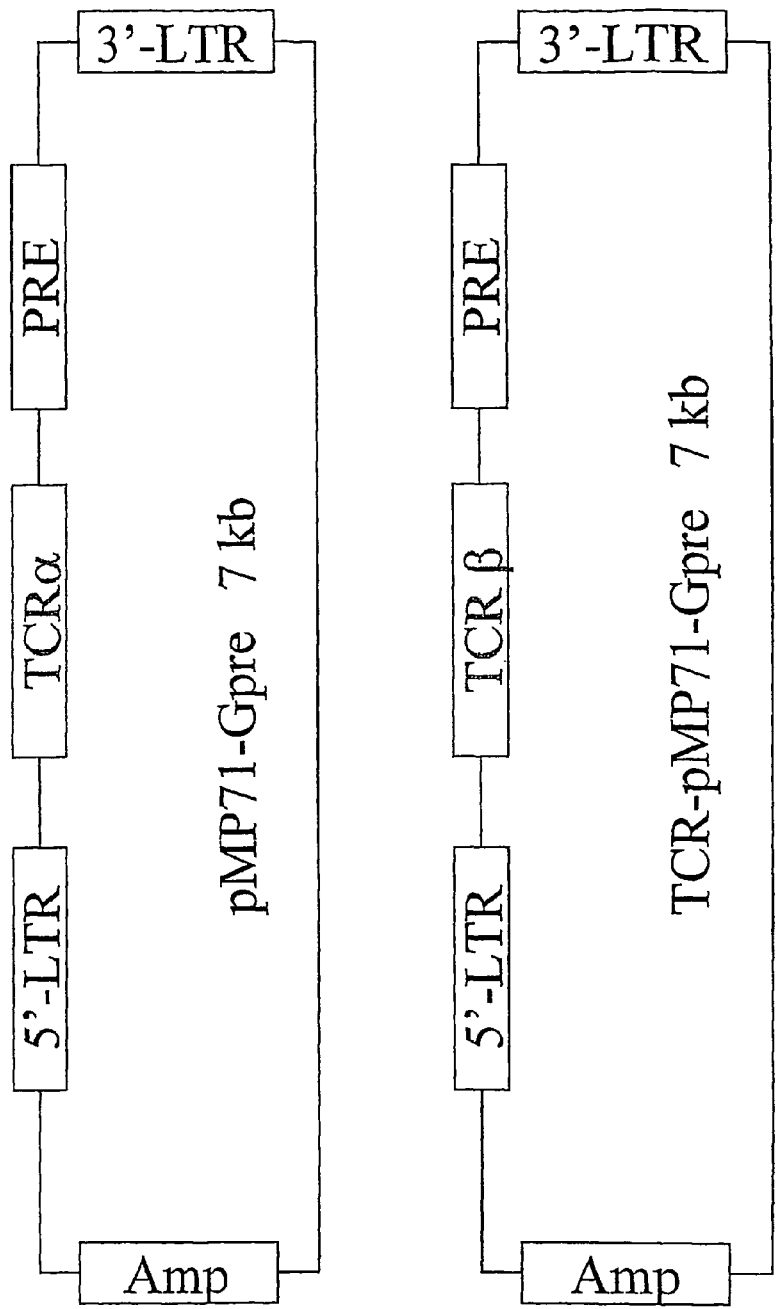

FIG. 7 is a diagram showing retroviral vectors containing TCR genes. The TCR alpha and beta chains were inserted into the retroviral vector pMP71 (Engels et al (2003) *Human Gene Ther.* 14, 1155-1168 for gene transfer into human T cells. LTR is a long terminated repeat. PRE is post transcriptional regulatory element.

Figure 8:
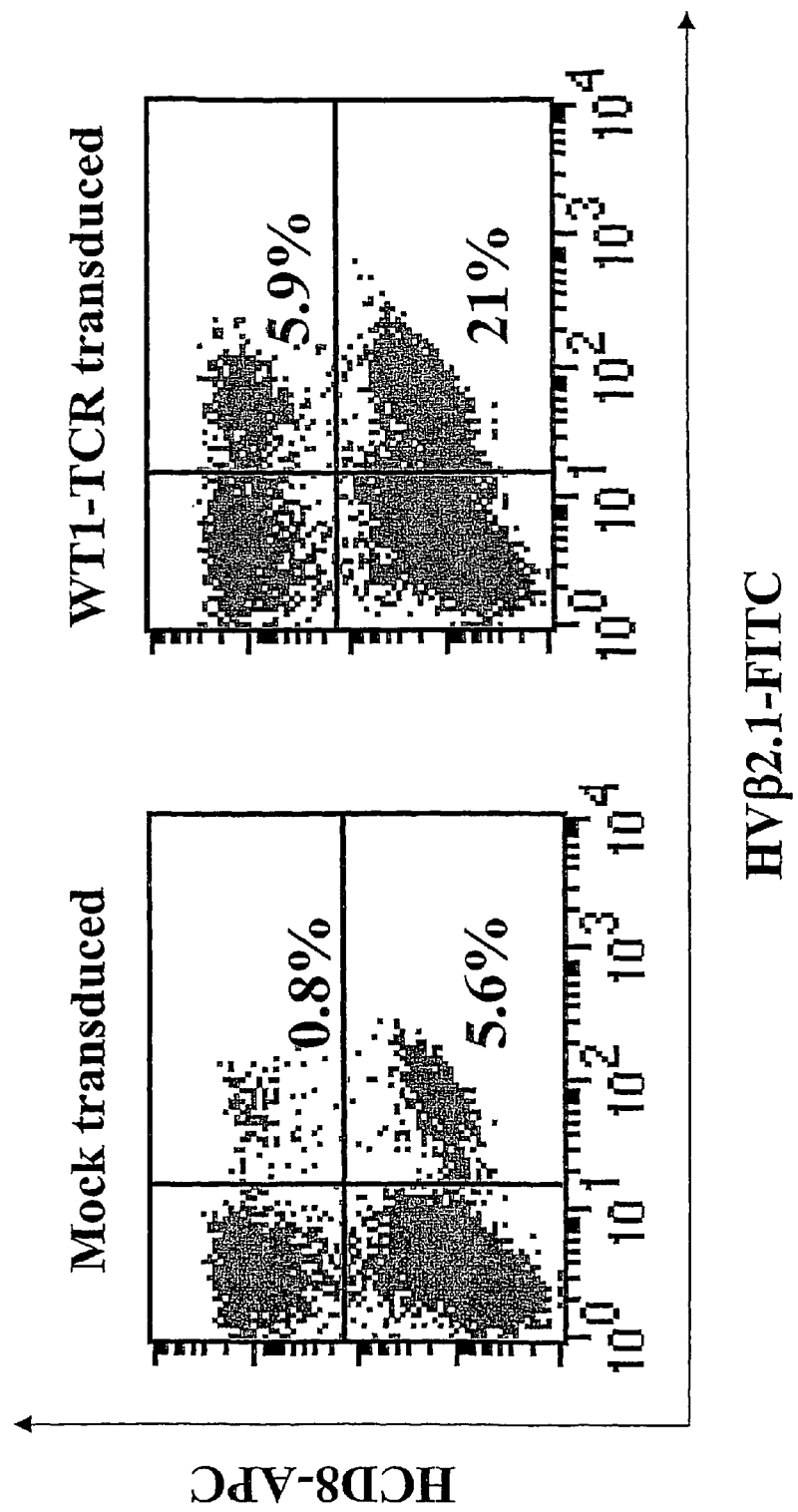

FIG. 8 is a diagram showing retroviral TCR gene transfer into human T cells. Peripheral blood lymphocytes were activated with anti-CD3 antibodies, IL-2 and IL-7, followed 3 days later by transduction with retroviral vectors encoding the WT1-specific TCR. TCR expression was monitored at day 6 using antibodies specific for the TCR-V-beta 2.1 (present in the transferred TCR). Mock transduced T cells show the percentage of un-manipulated human T cells expressing V-beta 2.1. After transduction both CD8-positive and CD8-negative (i.e. CD4-pos) T cells have an increased percentage of V-beta 2.1 cells. V-beta 2.1 DNA and amino acid sequences are shown in FIGS. 3 and 4.

Figure 9:
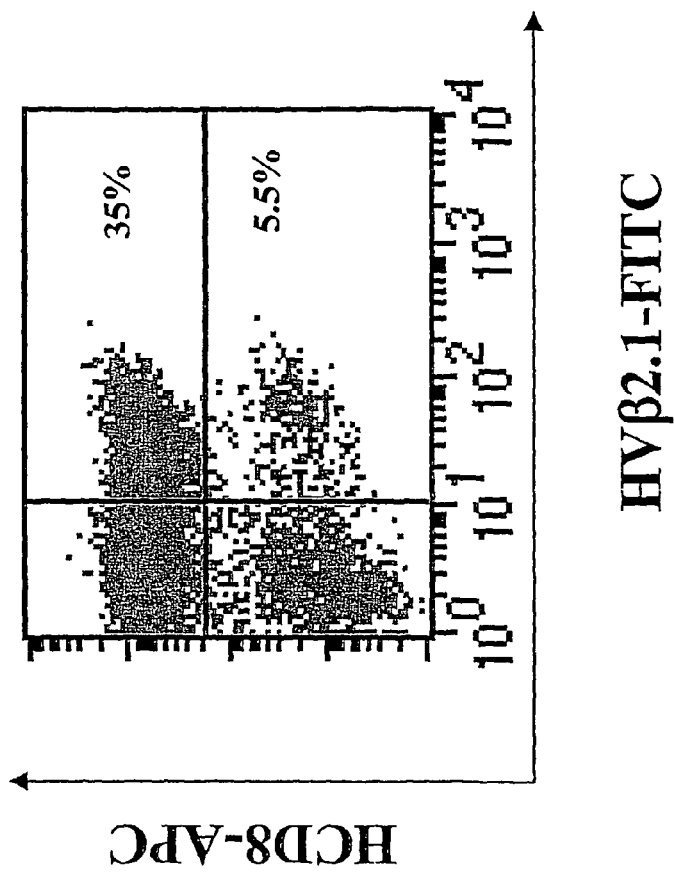

FIG. 9 shows that repeated stimulation of TCR-transduced T cells (as shown in FIG. 8) with T2 cells presenting the pWT126 peptide leads to an expansion of CD8-positive T cells expressing V-beta 2.1.

Figure 10:
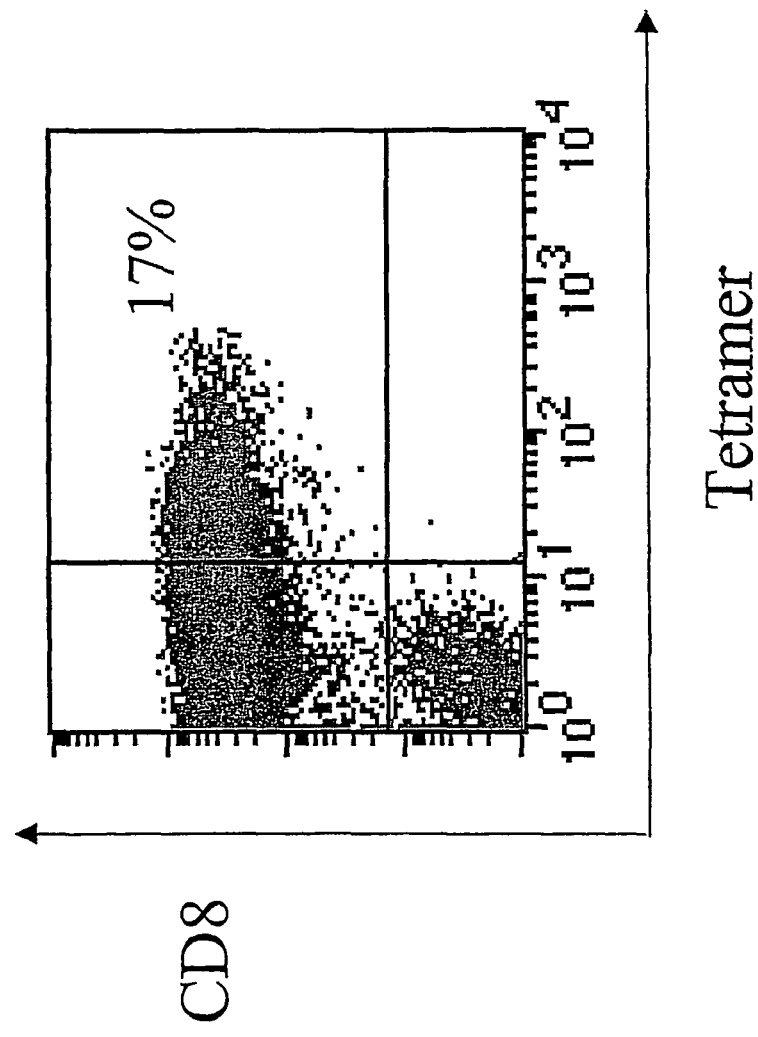

FIG. 10 shows that TCR-transduced T cells (as shown in FIGS. 8 and 9) stain with HLA-A2/pWT126 tetramers.

Figure 11:
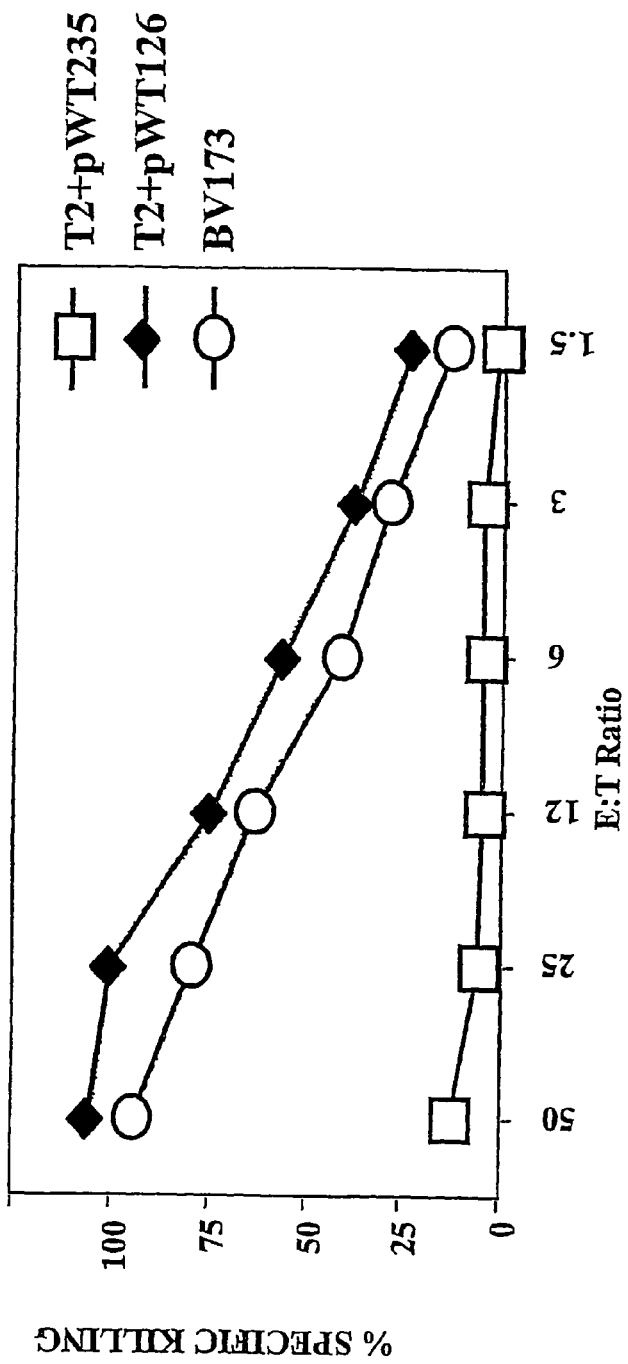

FIG. 11 shows that TCR-transduced T cells (as shown in FIGS. 8 and 9) kill the HLA-A2-positive T2 cells coated with the pWT126 peptide, but not T2 cells coated with the A2-binding pWT235 control peptide. The T cells also kill the HLA-A2-positive BV173 leukaemia cells expressing WT1 endogenously.

Figure 12:
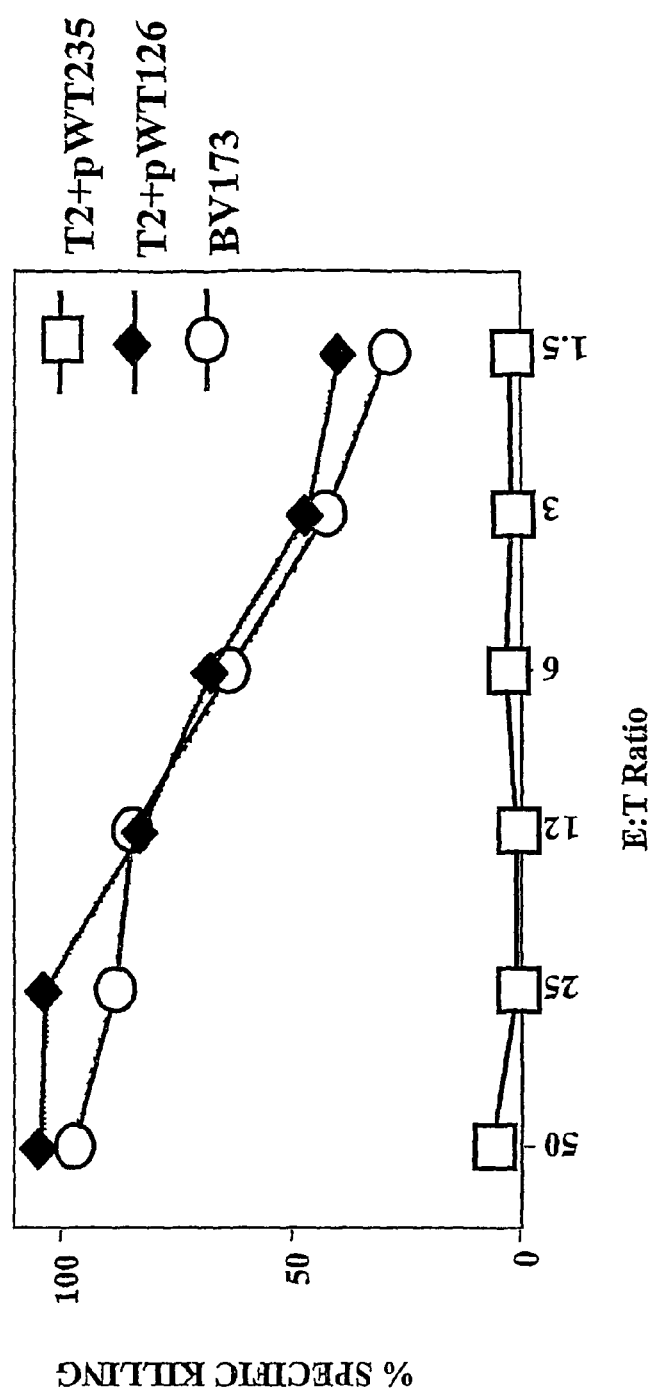

FIG. 12 shows that purified TCR-transduced CD8-positive T cells kill the HLA-A2-positive T2 cells coated with the pWT126 peptide, but not T2 cells coated with the A2-binding pWT235 control peptide. The CD8-positive T cells also kill the HLA-A2-positive BV173 leukaemia cells expressing WT1 endogenously.

Figure 13:
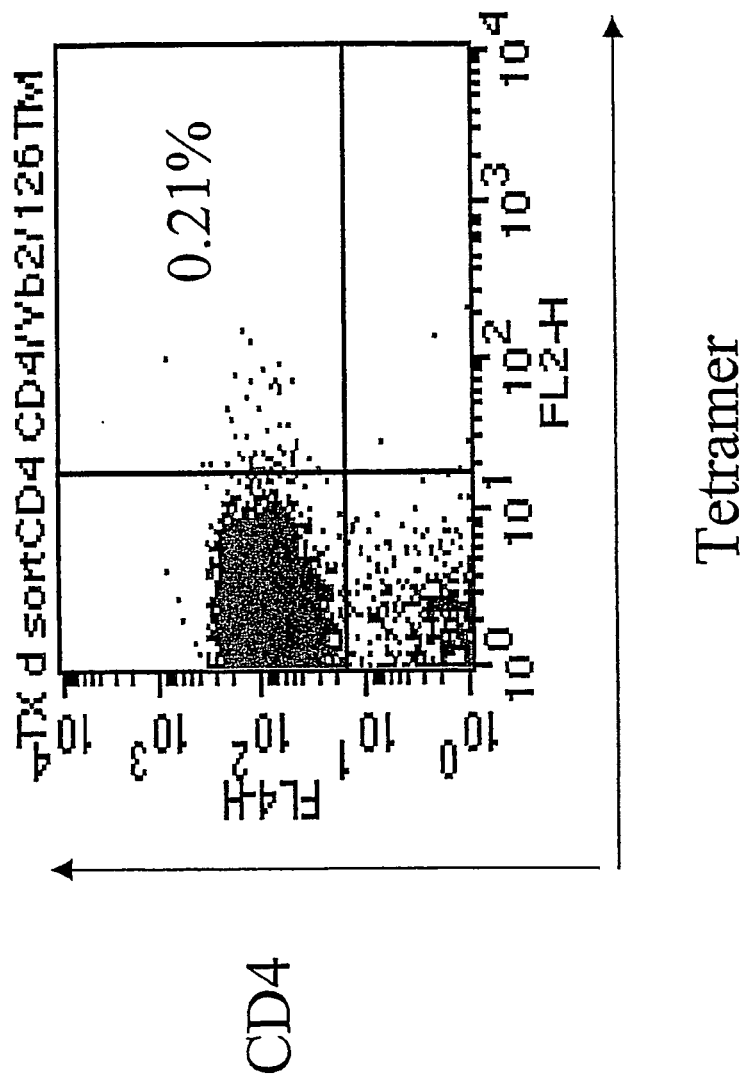

FIG. 13 shows that a small percentage of purified CD4-positive TCR-transduced T cells stain with HLA-A2/pWT126 tetramers.

Figure 14:
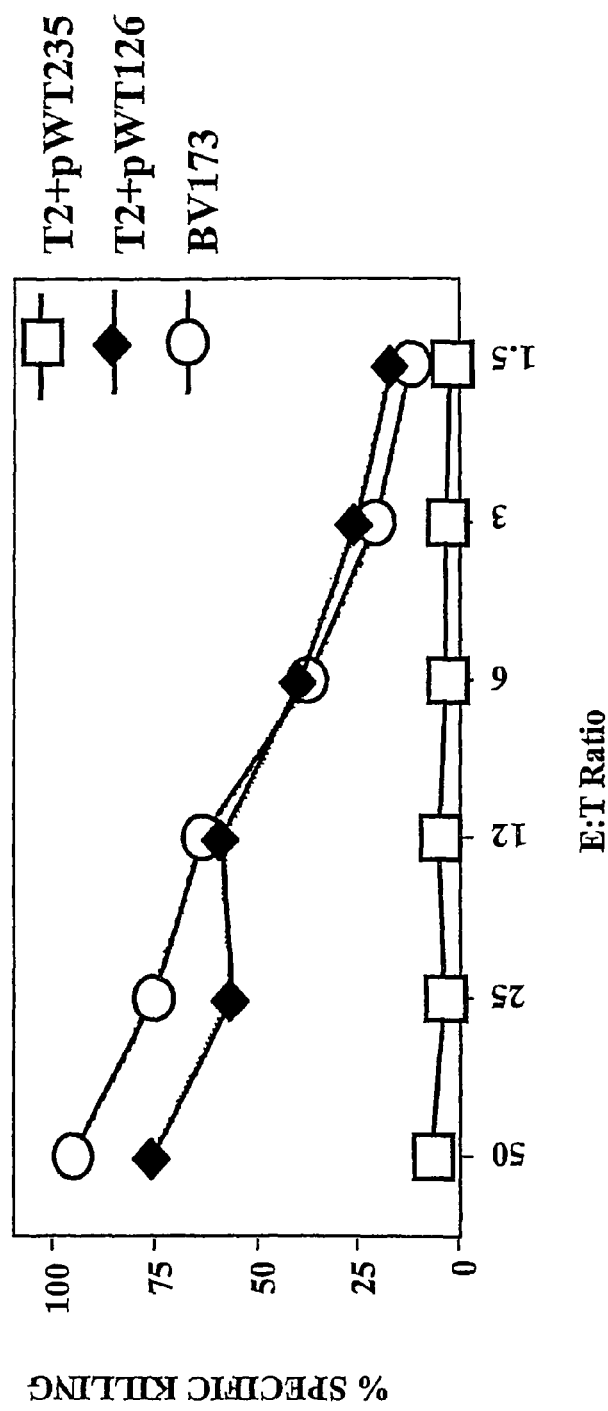

FIG. 14 shows that purified TCR-transduced CD4-positive T cells kill the HLA-A2-positive T2 cells coated with the pWT126 peptide, but not T2 cells coated with the A2-binding pWT235 control peptide. The CD4-positive T cells also kill the HLA-A2-positive BV173 leukaemia cells expressing WT1 endogenously.

Figure 15:
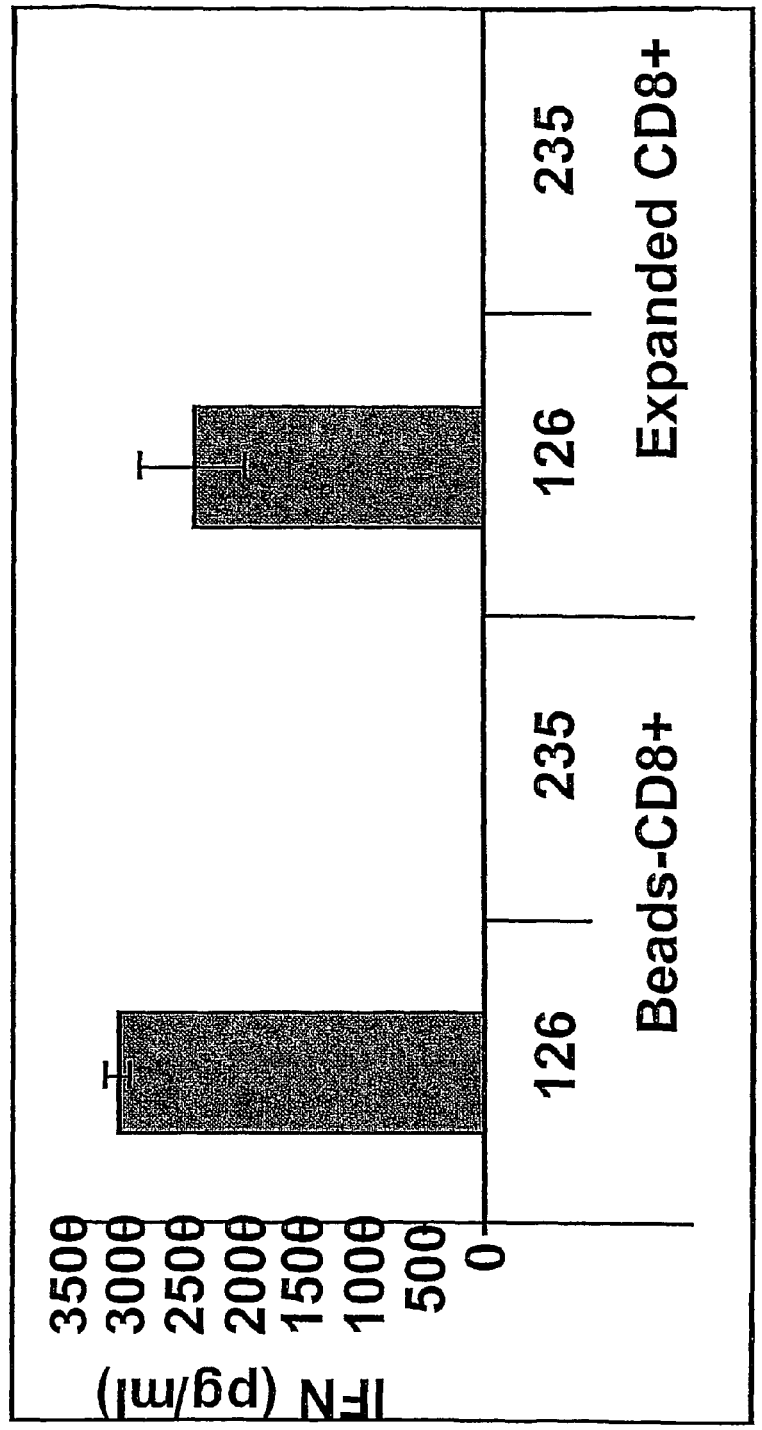

FIG. 15 shows that purified TCR-transduced CD8-positive T cells produce IFN-γ after stimulation with the HLA-A2-positive T2 cells coated with the pWT126 peptide, but not T2 cells coated with the A2-binding pWT235 control peptide. Also, the CD8-positive T cells produce IFN-γ after stimulation with the HLA-A2-positive BV173 leukaemia cells expressing WT1 endogenously.

Figure 16:
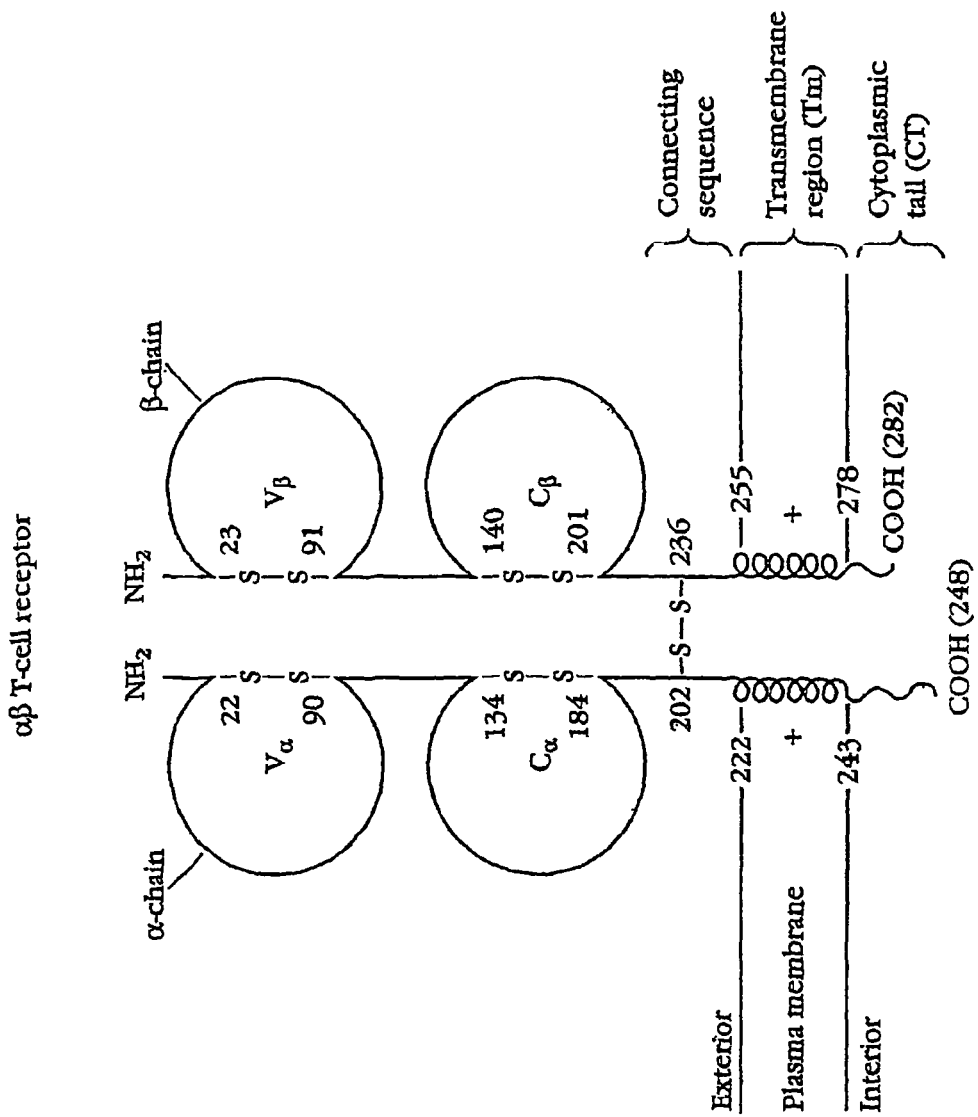

FIG. 16 is a schematic diagram showing the general structure of ββ TCR molecules. The amino acid numbers mentioned do not necessarily correspond to those in FIGS. 2 and 4.

SCHEDULE OF SEQ ID NOS.

1. RMFPNAPYL (SEQ ID NO: 1)
2. SSYSPS (SEQ ID NO: 2)
3. YTSAATL (SEQ ID NO: 3)
4. VVSPFSGGGADGLT (SEQ ID NO: 4)
5. SPFSGGGADGLT (SEQ ID NO: 5)
6. DFQATT (SEQ ID NO: 6)
7. SNEGSKA (SEQ ID NO: 7)
8. SARDGGEG (SEQ ID NO: 8)
9. RDGGEGSETQY (SEQ ID NO: 9)
10. FGKGTHLIIQP (SEQ ID NO: 10)
11. YIQNP (SEQ ID NO: 11)
12. SETQY (SEQ ID NO: 12)
13. FGPGTRLLVL (SEQ ID NO: 13)
14. EDLKN (SEQ ID NO: 14)
15. FIG. 1 nucleotide sequence (SEQ ID NO: 15)
16. FIG. 2 (and FIG. 5) amino acid sequence (SEQ ID NO: 16)
17. FIG. 3 nucleotide sequence (SEQ ID NO: 17)
18. FIG. 4 (and FIG. 6) amino acid sequence (SEQ ID NO: 18)

Example 1

Functionally Active T Cell Receptor (TCR) Specific for the WT-1-Derived Peptide pWT126 (RMFPNAPYL)

We have cloned a T cell receptor (TCR) that is specific for a peptide (pWT126; RMFPNAPYL) of the Wilms Tumour antigen-1 (WT1) presented by HLA-A2 class I molecules. The WT1 transcription factor is expressed in various human malignancies, including leukaemia, breast cancer, colon cancer, lung cancer, ovarian cancer and others. The CTL from which the TCR was cloned show killing activity against human cancer cells that express WT1, but not against normal human cells that express physiological levels of WT1.

The therapeutic goal is to equip patient T cells with this potent and specific killing activity by transfer of the genes encoding the TCR. For this, we have inserted the TCR genes into retroviral vectors and demonstrated that gene transduced human T cells show killing activity against WT1 expressing human cancer and leukemia cell lines. The specificity profile of this CTL line has been described in several research papers and can be summarized as: (1) Killing of HLA-A2-positive targets coated with the WT1-derived peptide pWT126 (Gao et al (2000) *Blood* 95, 2198-2203); (2) Killing of fresh HLA-A2-positive leukaemia cells expressing WT1 (Gao et al (2000) *Blood* 95, 2198-2203); (3) Killing of HLA-A2-positive leukemia CFU progenitor cells (Gao et al (2000) *Blood* 95, 2198-2203; Bellantuono et al (2002) 100, 3835-3837); (4) Killing of HLA-A2-positive leukaemia LTC-IC stem cells (Bellantuono et al (2002) *Blood* 100, 3835-3837); (5) Killing of HLA-A2-positive NOD/SCID leukaemia initiating cells (Gao et al (2003) *Transplantation* 75, 1429-1436); and (6) No killing of normal HLA-A2-positive NOD/SCID engrafting hematopoietic stem cells (Gao et al (2003) *Transplantation* 75, 1429-1436). We have now shown that human T cells transduced with the WT1-specific TCR display similar specificity as the CTL line from which the TCR was cloned.

The data described in detail in the legends to FIGS. 1 to 15 indicate that TCR gene transfer into human T cells is feasible and that it leads to the surface expression of the introduced TCR chains. The recipient T cells show killing activity against HLA-A2-positive targets coated with the pWT126 peptide. The TCR-transduced T cells also kill human tumour cells expressing WT1 endogenously. In addition, the transduced T cells produce IFN-g in an HLA-A2-restricted, peptide-specific fashion. Finally, the transferred TCR can function in CD4-positive helper T cells. These CD4-positive T cells show HLA-A2-restricted, antigen-specific killing activity and antigen-specific cytokine production (not shown).

This indicates that TCR gene transfer can be used to confer HLA class I-restricted antigen-specific effector function to both CD8-positive and CD4-positive human T cells.

Example 2

Selection and Treatment of a Patient

Peripheral blood monocyte cells (PBMCs) are taken from an HLA-A2-positive patient who has a WT1-expressing malignancy. The PBMCs are activated with anti-CD3/CD28 antibodies added to the culture or on beads for 3 days and then transduced with TCR encoding retroviral particles as described in Example 1. At day 5 we can demonstrate that transduced CD4 and CD8 T cells express the introduced TCR. At day 6 we can demonstrate antigen-specific activity of the transduced T cells. At day 6 the transduced T cells are reinfused into the patient.

The invention claimed is:

1. An isolated polynucleotide encoding a T cell receptor (TCR) alpha chain portion containing three alpha complementarity determining regions (CDRs):
CDR1α: SSYSPS (SEQ ID NO: 2);
CDR2α: YTSAATL (SEQ ID NO: 3); and
CDR3α: SPFSGGGADGLT (SEQ ID NO: 5),
wherein a TCR molecule containing the TCR alpha chain portion encoded by said polynucleotide and a TCR beta chain portion containing three beta CDRs:
CDR1β: DFQATT (SEQ ID NO: 6);
CDR2β: SNEGSKA (SEQ ID NO: 7); and
CDR3β: RDGGEGSETQY (SEQ ID NO: 9)
has affinity for an HLA-A2/RMFPNAPYL (SEQ ID NO: 1) complex.

2. An isolated polynucleotide encoding a T cell receptor (TCR) beta chain portion containing three beta complementarity determining regions (CDRs):
CDR1β: DFQATT (SEQ ID NO: 6);
CDR2β: SNEGSKA (SEQ ID NO: 7); and
CDR3β: RDGGEGSETQY (SEQ ID NO: 9),
wherein a TCR molecule containing the TCR beta chain portion encoded by said polynucleotide and a TCR alpha chain portion containing three alpha CDRs:
CDR1α: SSYSPS (SEQ ID NO: 2);
CDR2α: YTSAATL (SEQ ID NO: 3); and
CDR3α: SPFSGGGADGLT (SEQ ID NO: 5)
has affinity for an HLA-A2/RMFPNAPYL (SEQ ID NO: 1) complex.

3. An isolated polynucleotide encoding a single chain T cell receptor (TCR) molecule containing an alpha chain portion and a beta chain portion,
wherein the alpha chain portion contains three complementarity determining regions (CDRs):
CDR1α: SSYSPS (SEQ ID NO: 2);
CDR2α: YTSAATL (SEQ ID NO: 3); and
CDR3α: SPFSGGGADGLT (SEQ ID NO: 5),
and wherein the beta chain portion contains three CDRs:
CDR1β: DFQATT (SEQ ID NO: 6);
CDR2β: SNEGSKA (SEQ ID NO: 7); and
CDR3β: RDGGEGSETQY (SEQ ID NO: 9),
wherein the TCR molecule encoded by said polynucleotide has affinity for an HLA-A2/RMFPNAPYL (SEQ ID NO: 1) complex.

4. An expression vector comprising the polynucleotide according to any one of claims 1 to 3.

5. The expression vector according to claim 4 which is a retroviral vector.

6. A host cell comprising the polynucleotide according to any one of claims 1 to 3.

7. The host cell according to claim 6 which is a T cell.

8. The host cell according to claim 7 which is a T cell derived from a patient.

9. A host cell comprising the expression vector according to claim 4.

10. The host cell according to claim 9 which is a T cell.

11. The host cell according to claim 9 which is a T cell derived from a patient.

* * * * *

SEQUENCE LISTING

```
<160> NUMBER OF SEQ ID NOS: 18

<210> SEQ ID NO 1
<211> LENGTH: 9
<212> TYPE: PRT
<213> ORGANISM: Artificial Sequence
<220> FEATURE:
<223> OTHER INFORMATION: Peptide of WT1 which is presented by HLA-A2
      class I molecules

<400> SEQUENCE: 1

Arg Met Phe Pro Asn Ala Pro Tyr Leu
1               5

<210> SEQ ID NO 2
<211> LENGTH: 6
<212> TYPE: PRT
<213> ORGANISM: Artificial Sequence
<220> FEATURE:
<223> OTHER INFORMATION: CDR1  of human TCR V -1.5 (V -8.2)

<400> SEQUENCE: 2

Ser Ser Tyr Ser Pro Ser
1               5

<210> SEQ ID NO 3
<211> LENGTH: 7
<212> TYPE: PRT
<213> ORGANISM: Artificial Sequence
<220> FEATURE:
<223> OTHER INFORMATION: CDR2  of human TCR V -1.5 (V -8.2)

<400> SEQUENCE: 3

Tyr Thr Ser Ala Ala Thr Leu
1               5

<210> SEQ ID NO 4
<211> LENGTH: 14
<212> TYPE: PRT
<213> ORGANISM: Artificial Sequence
<220> FEATURE:
<223> OTHER INFORMATION: CDR3  of human TCR V -1.5 (V -8.2) - 1

<400> SEQUENCE: 4

Val Val Ser Pro Phe Ser Gly Gly Gly Ala Asp Gly Leu Thr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: CDR3  of human TCR V -1.5 (V -8.2) - 2

<400> SEQUENCE: 5

Ser Pro Phe Ser Gly Gly Gly Ala Asp Gly Leu Thr
```

```
<210> SEQ ID NO 6
<211> LENGTH: 6
<212> TYPE: PRT
<213> ORGANISM: Artificial Sequence
<220> FEATURE:
<223> OTHER INFORMATION: CDR1 of human TCR V -2.1 (V -20.1)

<400> SEQUENCE: 6

Asp Phe Gln Ala Thr Thr
1               5

<210> SEQ ID NO 7
<211> LENGTH: 7
<212> TYPE: PRT
<213> ORGANISM: Artificial Sequence
<220> FEATURE:
<223> OTHER INFORMATION: CDR2 of human TCR V -2.1 (V -20.1)

<400> SEQUENCE: 7

Ser Asn Glu Gly Ser Lys Ala
1               5

<210> SEQ ID NO 8
<211> LENGTH: 8
<212> TYPE: PRT
<213> ORGANISM: Artificial Sequence
<220> FEATURE:
<223> OTHER INFORMATION: CDR3 of human TCR V -2.1 (V -20.1) - 1

<400> SEQUENCE: 8

Ser Ala Arg Asp Gly Gly Glu Gly
1               5

<210> SEQ ID NO 9
<211> LENGTH: 11
<212> TYPE: PRT
<213> ORGANISM: Artificial Sequence
<220> FEATURE:
<223> OTHER INFORMATION: CDR3 of human TCR V -2.1 (V -20.1) - 2

<400> SEQUENCE: 9

Arg Asp Gly Gly Glu Gly Ser Glu Thr Gln Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Framework amino acid sequence of constant
      portion C-terminal to CDR3

<400> SEQUENCE: 10

Phe Gly Lys Gly Thr His Leu Ile Ile Gln Pro
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Beginning of constant region of human TCR V
      -1.5 (V -8.2)

<400> SEQUENCE: 11

Tyr Ile Gln Asn Pro
```

```
<210> SEQ ID NO 12
<211> LENGTH: 5
<212> TYPE: PRT
<213> ORGANISM: Artificial Sequence
<220> FEATURE:
<223> OTHER INFORMATION: Beginning of framework amino acid sequence of
      human TCR V -2.1 (V -20.1)

<400> SEQUENCE: 12

Ser Glu Thr Gln Tyr
1               5

<210> SEQ ID NO 13
<211> LENGTH: 10
<212> TYPE: PRT
<213> ORGANISM: Artificial Sequence
<220> FEATURE:
<223> OTHER INFORMATION: Part of framework amino acid sequence of human
      TCR V -2.1 (V -20.1)

<400> SEQUENCE: 13

Phe Gly Pro Gly Thr Arg Leu Leu Val Leu
1               5                   10

<210> SEQ ID NO 14
<211> LENGTH: 5
<212> TYPE: PRT
<213> ORGANISM: Artificial Sequence
<220> FEATURE:
<223> OTHER INFORMATION: Part of constant region of human TCR V -2.1
      (V -20.1)

<400> SEQUENCE: 14

Glu Asp Leu Lys Asn
1               5

<210> SEQ ID NO 15
<211> LENGTH: 830
<212> TYPE: DNA
<213> ORGANISM: Human TCR V -1.5 (V -8.2)

<400> SEQUENCE: 15
atgctcctgc tgctcgtccc agtgctcgag gtgatttta  ctctgggagg aaccagagcc     60
cagtcggtga cccagcttga cagccacgtc tctgtctctg aaggaacccc ggtgctgctg    120
aggtgcaact actcatcttc ttattccacca tctctcttct ggtatgtgca acaccccaac    180
aaaggactcc agcttctcct gaagtacaca tcagcggcca ccctggttaa aggcatcaac    240
ggttttgagg ctgaatttaa gagagtgaa acctccttcc acctgacgaa accctcagcc    300
catatgagcg acgcggctga gtacttctgt gttgtgagtc ttttttcagg aggaggtgct    360
gacggactca cctttggcaa agggactcat ctaatcatcc agccctatat ccagaaccct    420
gaccctgccg tgtaccagct gagagactct aaatccagtg acaagtctgt ctgcctattc    480
accgattttg attctcaaac aaatgtgtca caaagtaagg attctgatgt gtatatcaca    540
gacaaaactg tgctagacat gaggtctatg gacttcaaga gcaacagtgc tgtggcctgg    600
agcaacaaat ctgactttgc atgtgcaaac gccttcaaca cagcattat tccagaagac    660 accttcttcc ccagcccaga aagttcctgt gatgtcaagc tggtcgagaa aagctttgaa    720
acagatacga acctaaactt tcaaaacctg tcagtgattg gttccgaat cctcctcctg    780 aaagtggccg ggtttaatct gctcatgacg ctgcggctgt ggtccagctg                830
```

<210> SEQ ID NO 16
<211> LENGTH: 276
<212> TYPE: PRT
<213> ORGANISM: Human TCR V -1.5 (V -8.2)

<400> SEQUENCE: 16

Met Leu Leu Leu Leu Val Pro Val Leu Glu Val Ile Phe Thr Leu Gly
1               5                   10                  15

Gly Thr Arg Ala Gln Ser Val Thr Gln Leu Asp Ser His Val Ser Val
            20                  25                  30

Ser Glu Gly Thr Pro Val Leu Leu Arg Cys Asn Tyr Ser Ser Ser Tyr
        35                  40                  45

Ser Pro Ser Leu Phe Trp Tyr Val Gln His Pro Asn Lys Gly Leu Gln
    50                  55                  60

Leu Leu Leu Lys Tyr Thr Ser Ala Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Val Val
            100                 105                 110

Ser Pro Phe Ser Gly Gly Gly Ala Asp Gly Leu Thr Phe Gly Lys Gly
        115                 120                 125

Thr His Leu Ile Ile Gln Pro Tyr Ile Gln Asn Pro Asp Pro Ala Val
    130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
        275

<210> SEQ ID NO 17
<211> LENGTH: 933
<212> TYPE: DNA
<213> ORGANISM: Human TCR V -2.1 (V -20.1)

<400> SEQUENCE: 17
atgctgctgc ttctgctgct tctggggcca ggctccgggc ttggtgctgt cgtctctcaa      60
catccgagct gggttatctg taagagtgga acctctgtga agatcgagtg ccgttccctg     120
gactttcagg ccacaactat gttttggtat cgtcagttcc cgaaacagag tctcatgctg     180
atggcaactt ccaatgaggg ctccaaggcc acatacgagc aaggcgtcga aaggacaag      240 tttctcatca accatgcaag cctgaccttg tccactctga cagtgaccag tgcccatcct     300

-continued

```
gaagacagca gcttctacat ctgcagtgct agagatgggg gggagggttc ggagacccag    360
tacttcgggc caggcacgcg gctcctggtg ctcgaggacc tgaaaaacgt gttcccaccc    420
gaggtcgctg tgtttgagcc atcagaagca gagatctccc acacccaaaa ggccacactg    480
gtgtgcctgg ccacaggctt ctaccccgac cacgtggagc tgagctggtg ggtgaatggg    540
aaggaggtgc acagtggggt cagcacagac ccgcagcccc tcaaggagca gcccgccctc    600
aatgactcca gatactgcct gagcagccgc ctgagggtct cggccacctt ctggcagaac    660
ccccgcaacc acttccgctg tcaagtccag ttctacgggc tctcggagaa tgacgagtgg    720
acccaggata gggccaaacc tgtcacccag atcgtcagcg ccgaggcctg ggtagagca    780 gactgtggct tcacctccga gtcttaccag caaggggtcc tgtctgccac catcctctat    840
gagatcttgc tagggaaggc caccttgtat gccgtgctgg tcagtgccct cgtgctgatg    900
gccatggtca agagaaagga ttccagaggc tag                                 933
```

```
<210> SEQ ID NO 18
<211> LENGTH: 310
<212> TYPE: PRT
<213> ORGANISM: Human TCR V -2.1 (V -20.1)

<400> SEQUENCE: 18

Met Leu Leu Leu Leu Leu Leu Gly Pro Gly Ser Gly Leu Gly Ala
1               5                   10                  15

Val Val Ser Gln His Pro Ser Trp Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Arg Asp
            100                 105                 110

Gly Gly Glu Gly Ser Glu Thr Gln Tyr Phe Gly Pro Gly Thr Arg Leu
        115                 120                 125

Leu Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270
```

```
Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Ser Arg Gly
305                 310
```